(12) United States Patent  
Calvosa et al.

(10) Patent No.: US 9,145,543 B2  
(45) Date of Patent: Sep. 29, 2015

(54) PROCESS FOR CULTURING ADHERENT CELLS

(75) Inventors: Eric Calvosa, Haute Rivoire (FR); Nicolas Seve, Chambost Longessaigne (FR)

(73) Assignee: Sanofi Pasteur SA, Lyons (FR)

(*) Notice: Subject to any disclaimer, the term of this patent is extended or adjusted under 35 U.S.C. 154(b) by 0 days.

(21) Appl. No.: 12/976,679

(22) Filed: Dec. 22, 2010

(65) Prior Publication Data

US 2011/0151506 A1 Jun. 23, 2011

Related U.S. Application Data

(60) Provisional application No. 61/358,390, filed on Jun. 24, 2010.

(30) Foreign Application Priority Data

Dec. 23, 2009 (FR) ...................................... 09 59472  
Mar. 11, 2010 (FR) ...................................... 10 51754

(51) Int. Cl.
| | |
|---|---|
| *C12P 1/00* | (2006.01) |
| *C12N 1/00* | (2006.01) |
| *C12N 5/00* | (2006.01) |
| *C12N 7/00* | (2006.01) |

(52) U.S. Cl.  
CPC .. *C12N 5/00* (2013.01); *C12N 7/00* (2013.01); *C12N 2500/99* (2013.01); *C12N 2760/20151* (2013.01)

(58) Field of Classification Search  
None  
See application file for complete search history.

(56) References Cited

U.S. PATENT DOCUMENTS

| 5,714,375 | A  | * | 2/1998 | Knittel et al. | 435/252.1 |
| 6,020,182 | A  | * | 2/2000 | Cates et al.   | 435/235.1 |
| 6,168,944 | B1 | * | 1/2001 | Condon et al.  | 435/239   |
| 6,951,752 | B2 | * | 10/2005 | Reiter et al. | 435/235.1 |
| 2002/0119567 | A1 | * | 8/2002 | Chiarello et al. | 435/404 |
| 2003/0049276 | A1 | * | 3/2003 | Klein et al.   | 424/211.1 |

(Continued)

OTHER PUBLICATIONS

Calvosa, 6th Annual IBC Presentation, Slides 1-32, San Diego (Jun. 2009).*

(Continued)

*Primary Examiner* — Robert Mondesi  
*Assistant Examiner* — Thomas J Visone  
(74) *Attorney, Agent, or Firm* — McDonnell Boehnen Hulbert & Berghoff LLP (57) ABSTRACT

The subject of the present invention is a process for producing adherent cells comprising:
 a. introducing a suspension of adherent cells into a culture vessel containing microcarriers in a culture medium;
 b. amplifying the cells by performing a plurality of cell passages in the same culture vessel wherein each cell passage subsequent to the first is carried out:
  i) by using all or part of the cells produced during the previous cell passage after having subjected the cells to enzyme treatment to detach the cells from the microcarriers, and
  ii) by introducing culture medium and an increasing amount of microcarriers into the culture medium; and
 c. harvesting the cells produced during the last cell passage, optionally after having subjected the cells to enzyme treatment to detach cells from microcarriers.

The invention also relates to the implementation of this process for the production of biological agents, serving in particular to prepare vaccines or drugs.

23 Claims, 2 Drawing Sheets

(56) References Cited

U.S. PATENT DOCUMENTS

2003/0108861 A1* 6/2003 Meyer et al. .................. 435/5
2007/0264713 A1* 11/2007 Terstegge et al. ............. 435/383

OTHER PUBLICATIONS

Forestell et al., App. Microbiol. Biotechnol., 38: 165-172 (1992).*
Lakhotia et al., Biotechnol Bioeng., vol. 39, 95-107 (1992).*
Lonza PowerPoint 2005.*
Mendonca et al (Bioproc. Eng. 20:565-571 (1999).*
Chengzu, X. et al., "High density cultivation of genetically-engineered CHO cell lines with microcarrier culture systems", Chinese Medical Sciences Journal, 1994, 9(2), 71-74.
Ohlson, S. et al., "Bead-to-bead transfer of Chinese hamster ovary cells using macroporous microcarriers", Cytotechnology, 1994, 14(1), 67-80.
Wang, Y. et al., "Bead-to-bead transfer of Vero cells in microcarrier culture", Cytotechnology, 1999, 31(3), 221-224.
Rourou, S. et al., "A novel animal-component-free medium for rabies virus production in Vero cells grown on Cytodex 1 microcarriers in a stirred bioreactor", Applied Microbiology and Biotechnology, 2009, 85(1), 53-63.
He et al., "Serum-free culture of Vero cells and influenza virus on microcarriers," Chin J Biologicals, Feb. 2007, vol. 20, No. 2, pp. 125-134.
Xiao et al., "High density and scale-up cultivation of recombinant CHO cell line and hybridomas with porous microcarrier Cytopore," Cytotechnology 30:143-147, 1999.
Chengzu et al., "High Density Cultivation of a Recombinant CD-1 Cell Line Producing prourokinase Using a Biosilon Microcarrier Culture System," Chin Med Sci J, 1994, vol. 9, No. 1, pp. 203-208.
Aunins, "Viral Vaccine production in Cell Culture," Encyclopedia of Industrial Biotechnology, Bioprocess, Bioseparation, and Cell Technology, vols. 1-7, 2010, pp. 4789-4817.
Wang et al., "Bead-to-bead transfer of Vero cells in microcarrier culture," Cytotechnology 31:221-224, 1999.
Madeline, Brice et al., "Culturing a Duck ES-Derived Cell Line in Single-Use Bioreactors," BioProcess International, Mar. 2015, pp. 26-33.

* cited by examiner

PROCESS FOR CULTURING ADHERENT CELLS

CROSS-REFERENCE TO RELATED APPLICATIONS

This application claims the benefit of priority of U.S. provisional application 61/358,390, filed Jun. 24, 2010, French patent application no 10 51754, filed Mar. 11, 2010 and French patent application no 09 59472, filed Dec. 23, 2009.

BACKGROUND OF THE INVENTION

1. Field of the Invention

The subject of the invention is a process for producing adherent cells to microcarriers, according to which adherent cells are introduced into a culture vessel which contains microcarriers in a culture medium, and a plurality of cell passages is carried out in the same vessel, each time using all or part of the cells of the preceding cell passage for carrying out the next cell passage. The invention also relates to the implementation of this process for the production of biological agents, used in particular to prepare vaccines or drugs.

2. Summary of the Related Art

In the 1980s, the development of the technology of cell culture on microcarriers facilitated the large-scale production of adherent cells and consequently the production of biological agents. The production of adherent cells intended for the production of biological agents for pharmaceutical use must nevertheless observe a certain number of regulatory constraints, among which the prohibition of the use of adherent cells beyond a certain number of "cell passages" because of the risk of morphological and/or biological transformation of the cells. This is in particular the case of cells of the Vero line.

U.S. Pat. No. 4,664,912 describes a process that is convenient at an industrial scale for producing an industrial batch of cells from a cell seed originating from a working cell bank. It is based on a succession of cell passages, each in different bioreactors, the working volumes of which increase during the successive cell passages. This makes it possible each time to increase the amount of microcarriers while at the same time maintaining an optimal concentration of microcarriers in the culture medium that is usually comprised between 1 and 5 g/l. The cell biomass thus increases during the successive cell passages until the desired industrial batch of cells is obtained. The transfer of the cells from one bioreactor to another bioreactor is carried out after having detached the adherent cells from their microcarriers by means of treatment with trypsin and then by blocking the action of the enzyme by introducing serum proteins or serum into the medium so as to preserve as much as possible the integrity of the cells. The cell suspension obtained is then transferred (in the presence or absence of the used microcarriers) into a larger bioreactor which contains a greater amount of naked microcarriers. However, this method of industrial production of adherent cells requires the use and the handling of a large amount of material, which has an impact on the production costs for the biological agents.

In order to reduce the production costs for adherent cells intended for the production of biological agents, EP 1060241 proposes a faster production method that no longer requires the production to be reinitiated from a cell seed originating from a working bank each time it is desired to obtain an industrial batch of cells. The method consists in transferring, after each cell passage, most of the cells (80 to 90% of the cell biomass) to one or more other bioreactors so as to continue to amplify the cell biomass and to constitute an industrial production batch of cells, while the remaining 10 to 20% of the cells are maintained so as to keep a stock "of feeder cells" from which further batches of cells can be produced. This method nevertheless has the following drawbacks:

- the cell batches produced display a certain heterogeneity insofar as they do not all have the same number of cell passages.
- The maintaining of a stock of "feeder" cells in culture at the time of each transfer operation inevitably leads to an "aging" of the cells which is directly linked to the number of cell passages carried out, and can therefore be used only for a limited period of time for the regulatory reasons already mentioned.

To avoid the use of a proteolytic enzyme such as trypsin that is detrimental to cell integrity, Ohlson et al in Cytotechnology (1994), vol 14, p 67-80 describes a "bead to bead cell transfer" technology in the absence of any proteolytic enzyme treatment. The close contact between microcarriers covered by adherent cells and naked microcarriers favours the transfer of cells to the naked microcarriers where the cells can proliferate. Therefore, to increase cell growth, naked microcarriers are added to the culture medium containing microcarriers covered by adherent cells while stirring intermittently the medium to favour the contact between the microcarriers. Nevertheless the cell population which is obtained is dissynchronised with cells in various stages of the cell cycle. This can be of major concern for the production of biological agents.

SUMMARY OF THE INVENTION

In view of the foregoing, we recognized a need to optimize the methods of large-scale production of adherent cells and also the production of biological agents derived therefrom so as to reduce production costs.

To this effect, the subject of the present invention comprises a process for producing adherent cells by performing a plurality of cell passages in a single culture vessel wherein each cell passage subsequent to first cell passage is carried out following treatment of the cells with a proteolytic enzyme. The present invention also comprises using the aforementioned method for producing biological agents from the cells. We have found that the process of the invention is able to amplify the initial adherent cell population by a factor of about 60 or more and can be conducted at very large scale.

BRIEF DESCRIPTION OF THE DRAWINGS

FIG. 1a displays the conventional prior art process wherein the successive cell passages are conducted in different culture vessels of increasing working volume, And FIG. 1b displays the process according to the invention ("all-in-one process") wherein the successive cell passages are carried out in a single culture vessel.

DETAILED DESCRIPTION OF THE PREFERRED EMBODIMENTS

In one aspect, the invention comprises
A process for producing adherent cells, comprising:
a. introducing a suspension of adherent cells into a culture vessel containing microcarriers in a culture medium;
b. amplifying the cells by performing a plurality of cell passages in the same culture vessel wherein each cell passage subsequent to the first cell passage is carried out:
   i. by using all or part of the cells produced during the previous cell passage after having subjected the cells to enzyme treatment to detach the cells from the microcarriers, and
   ii. by introducing culture medium and an increasing amount of microcarriers; and
c. harvesting the cells produced during the last cell passage, optionally after having subjected the cells to enzyme treatment to detach cells from microcarriers.

The subject of the present invention is also:
A process for producing a biological agent from adherent cells, comprising:
a. introducing adherent cells into a culture vessel containing microcarriers in a culture medium;
b. amplifying the cells by performing a plurality of cell passages in the same culture wherein each cell passage subsequent to the first cell passage is carried out:
   i. by using all or part of the cells produced during the previous cell passage after having subjected the cells to enzyme treatment to detach the cells from the microcarriers, and
   ii. by introducing culture medium and an increasing amount of microcarriers; and
c. treating the cells produced during the last cell passage such that it produces the biological agent, wherein said treating is carried out in the same culture vessel as the one used to amplify the cells; and
d. harvesting the biological agent.

According to one aspect of the process for producing the biological agent, the biological agent is an infectious agent and the treatment of the cells is carried out by infecting the cell population with said infectious agent in an infection medium.

According to one particular aspect, the infectious agent is rabies virus and the infection medium is a viral infection medium free of any product of animal origin.

Generally, the number of cell passages carried out in the same culture vessel is 2, 3 or 4.

The microcarrier concentration in the culture medium during the first cell passage is usually <1 g/l, and preferably ≤0.5 g/l.

Typically, at the end of each cell passage, the enzyme treatment employs a solution containing a proteolytic enzyme, such as trypsin.

According to another aspect of the process according to the invention, each cell passage subsequent to the first cell passage is carried out by increasing the volume of the culture medium.

Preferably, the first cell passage is carried out in a volume of culture medium that is between ⅕ and half the working volume of the culture vessel.

In another embodiment of the process according to the invention, the culture medium is free of serum of animal origin.

Preferably, the culture medium is free of products of animal origin.

According to another aspect, the protein concentration in the culture medium is ≤15 mg/l. Preferably, the proteins are not of animal origin.

According to yet another aspect, the culture medium contains a cell protection agent.

Preferably, the cell protection agent is a polyvinylpyrrolidone or a poloxamer.

According to yet another embodiment of the process according to the invention, the culture vessel is a bioreactor that has a working volume of between 3 and 3000 liters, preferably between 20 and 1000 liters, and particularly preferably between 20 and 500 liters.

In another embodiment of the process according to the invention, the culture vessel is a disposable bioreactor.

In one particular aspect of the process according to the invention, the adherent cells are Vero cells.

In general, the cell population that is harvested according to the process of the invention contains at least 60 times more cells than the number of cells that were initially introduced into the culture vessel.

In another aspect, the invention comprises a process for producing cells adherent to microcarriers, comprising:
a. thawing a stock of adherent cells, and then
b. subjecting the thawed adherent cells to the process of the invention.

In yet another aspect, the invention relates to a process for producing adherent cells, further comprising:
a. transferring the cells harvested during the last cell passage carried out in a first culture vessel, which cells have been subjected to enzyme treatment to detach the cells from the microcarriers, into a second culture vessel, the working volume of which is larger than the working volume of the first culture vessel and that contains a culture medium containing microcarriers in a larger amount than the amount of microcarriers that was present during the last cell passage carried out in the first culture vessel, and
b. performing the amplification and harvesting of the cell population according to the process of the invention on the cells transferred into the second culture vessel.

The invention also comprises the use of adherent cells that have been produced by the process of the invention for the production of biological agents.

Lastly, the invention comprises a process for producing cells adherent to microcarriers in a culture medium, according to which the amount of cells produced is increased by a factor ≥60 by carrying out a plurality of cell passages in a single culture vessel.

The invention comprises a process for producing adherent cells according to which, in order to amplify cells and form industrial cell batches, a plurality of cell passages is carried out in one and the same cell culture vessel. Owing to this process, the number of culture vessels used is reduced and the cell batches produced are more homogeneous than prior art methods because they all have the same number of cell passages. This process is also used for the production of biological agents.

For the purpose of the invention, a "cell passage" begins at the time a suspension of adherent cells is brought into contact with microcarriers in a culture medium and usually ends at the time the adherent cells are freed from their microcarriers by enzyme treatment and are again in the form of a suspension of adherent cells in the culture medium (although harvesting of adherent cells bound to the microcarriers is also contemplated). A cell passage usually comprises the following phases:

a microcarrier colonization phase, which corresponds to the period of time during which the suspension of cells which have been brought into contact with the suspension of microcarriers in the culture medium adhere to the microcarriers;

a phase of amplification of the adherent cells on the microcarriers, which corresponds to the period of time during which the cells grow on the microcarriers until the available surface of the colonized microcarriers is more than 70%, and preferably more than 80%, covered by the cells. When the cells have covered more than 70% of the available surface of the colonized microcarriers, the adherent cells are considered to be "substantially confluent" or to have reached the "stage of confluence"; and a phase of detachment of a majority of the substantially confluent cells from their microcarriers by enzyme treatment (in general more than 80% and preferably more than 90% of the cells are detached) in a short space of time (in general in less than 30 minutes and often in a period of time of less than 20 minutes). The cell population is thus essentially in the form of a suspension of cells freed from their microcarriers (or detached from their microcarriers).

Depending on the intended use of the adherent cells which are produced, the last cell passage carried out in the culture vessel may or may not comprise a detachment phase.

In the context of the present invention, the successive cell passages are carried out in the same culture vessel, using all or part of the cells obtained during the previous cell passage for carrying out the next cell passage. In general, at least 80% of the cells obtained during the previous cell passage is used to carry out the next cell passage. Preferably, in order to maximize the number of cells produced, each successive cell passages is carried out by using the entire cell population obtained during the previous cell passage. Even if at the end of each cell passage there is an enzymatic treatment to detach (or release) the cells from their microcarriers, there is no transfer of the cells into one or more other cell culture vessels in order to continue to amplify the cells, contrary to the prior art. The amplification of the cells is carried out according to the invention in a single culture vessel. Furthermore, an amount of cells equivalent to the prior art are produced in the same range of time using the process of the invention without handling several culture vessels, which in turn lessens the space needed to produce industrial batches of cells and ultimately reduces the production costs. Surprisingly, although the cell amplification requires an enzymatic treatment at each cell passage, the amount of cells that is produced at the end of the process according to the invention is significantly larger that the amount obtained using the conventional "bead-to-bead transfer" technology. (cf. example 2).

Each new cell passage (meaning each cell passage subsequent to the first cell passage) is carried out in the same culture vessel. To start up a cell passage subsequent to the first cell passage, an amount of microcarriers larger than the amount of microcarriers that was introduced during the previous cell passage is introduced so as to increase the available surface area of the cell support. For the purpose of the invention, it is understood that the term "new cell passage" or "cell passage subsequent to the first cell passage" refers to a cell passage that is consecutive to a cell passage that was previously carried out in the culture vessel. It is also understood that the introduction or the addition of microcarriers in the culture vessel corresponds to the introduction or addition of naked microcarriers. Preferably, unused microcarriers are used to facilitate the adhesion of adherent cells. Even if generally the volume of culture medium is concomitantly increased at each cell passage subsequent to the first cell passage, the increased amount of microcarriers is usually proportionally greater than the increase in volume of medium. Usually it results in a gradual increase in the microcarrier concentration in the culture medium during each successive cell passages. During the last cell passage, when, for instance, dextran based microbeads (Cytodex™ 1, 2 or 3) are used, the microcarrier concentration is generally between 1 and 7 g/l but may reach 10 to 15 g/l. The process of the invention according to which the cells are amplified by successive cell passages in one and the same culture vessel is also called "all-in-one process" (see FIG. 1b).

Usually, two, three, or four cell passages are carried out in the same culture vessel. Depending on the subsequent use which is made thereof, the cells that are harvested are either in the form of a suspension of cells released from their microcarrier (in this case, the last cell passage is carried out with the cell detachment step being included) or in the form of a suspension of cells adherent to the microcarriers (in this case, the last cell passage is carried out with the cell detachment step being omitted).

When the process for producing adherent cells comprises two successive cell passages carried out in one and the same culture vessel, the process according to the invention amounts to performing the following steps:

a. introducing culture medium, microcarriers and adherent cells into a culture vessel;

b. subjecting the cells to culture conditions that allow the cells to adhere to the microcarriers and to proliferate on the microcarriers;

c. detaching the cells from their microcarriers by means of an enzyme treatment and optionally withdrawing a portion of them from the culture vessel;

d. introducing again culture medium and microcarriers such that the amount of microcarriers that is introduced is higher than the amount of microcarriers that was previously introduced, e. again subjecting the cells to culture conditions that allow the cells to adhere to the microcarriers and to proliferate on the microcarriers; and f. harvesting the cells that are obtained after optionally having detached the cells from their microcarriers by means of an enzyme treatment; said steps a) to e) being conducted in one and the same culture vessel.

Parts a) to c) correspond to the first cell passage and parts d) to f) to the second cell passage which ends by the harvest of the cells.

When there are more than two successive cell passages conducted in the same culture vessel, it amounts, after part e) is performed, to repeating at least once again parts c), d) and e) in the same culture vessel before proceeding to part f). Usually, parts c), d) and e) are repeated once or twice, which corresponds to a total of three or four cell passages, respectively. Preferably, part c) is performed when the cells are substantially confluent. Usually, the volume of culture medium is increased each time culture medium and microcarriers are added (part d)).

When the cells that are harvested at the end of the process according to the invention are used to constitute a cell stock, the last cell passage generally comprises a cell detachment step by means of an enzyme treatment that is usually carried out in the same culture vessel. The cell population that is harvested is then essentially in the form of a suspension of cells freed from their microcarriers.

When the cells are used for the production of a biological agent, the last cell passage is often carried out without including a cell detachment step. The cells produced in the form of a suspension of cells adherent to the microcarriers are then treated directly in the same culture vessel to produce the biological agent of interest. The "biological agent" is intended to mean any substance or organism which can be produced by the adherent cells. They include, for example, viruses and proteins (e.g., antibodies, antigens, enzymes, etc.). When the process for producing a biological agent by adherent cells comprises two successive cell passages carried out in the same culture vessel, the process according to the invention amounts to performing the following steps:

a. introducing culture medium, microcarriers, and adherent cells into a culture vessel;
b. subjecting the cells to culture conditions that allow the cells to adhere to the microcarriers and to proliferate on the microcarriers;
c. detaching the cells from their microcarriers by means of an enzyme treatment and optionally withdrawing a portion of them from the culture vessel;
d. introducing again culture medium and microcarriers into the culture vessel such that the amount of microcarriers that is introduced is higher than the amount of microcarriers that was previously introduced;
e. again subjecting the cells to culture conditions that allow the cells to adhere to the microcarriers and to proliferate on the microcarriers;
f. treating the cell population such that it produces the biological agent; and
g. harvesting the biological agent, said steps a) to f) being carried out in one and the same culture vessel.

When there are more than two successive cell passages carried out in the same culture vessel, it amounts, after part e) is performed, to repeating at least once again parts c), d) and e) before proceeding to part f). Usually, parts c), d) and e) are repeated once or twice, which corresponds to a total of three or four cell passages, respectively.

When the biological agent to be produced is a recombinant protein (e.g., a cytokine, an antibody, or a vaccine protein), the cell suspension is placed under culture conditions that promote the production of this protein using suitable production media. By way of example, the media described in EP 0354129 for the production of recombinant proteins by CHO cells and Vero cells can be used.

When the biological agent is an infectious agent, the suspension of cells adherent to the microcarriers is infected by introducing the infectious agent (e.g., bacteria, viruses, parasites, etc.) into the culture vessel after having generally replaced the culture medium with an infection medium. The infectious biological agent may in particular be a recombinant virus (e.g., recombinant poxviruses, recombinant adenoviruses) or viruses such as, for example, rabies virus, influenza virus, poliovirus, etc. The biological agent is usually harvested by sampling the culture supernatant one or more times—see Example 7—. When the biological agent is rather intracellular (for instance non-lytic viruses), it is often advantageous to harvest the supernatant and the cells, which are subsequently treated with lytic agents.

The media used for the production of biological agents, in particular the infection media used for the production of viruses such as rabies virus, may be advantageously free of serum of animal origin, of protein of animal origin, or even of any product of animal origin.

The microcarriers suitable for the subject of the invention are usually in the form of microbeads, which are preferably nonporous so as to facilitate the action of the enzymes. They have a diameter preferably between 90 and 250 μm. Their density is slightly higher than that of the culture medium so as to facilitate their recovery by simple settling out, but at the same time it should not be so high as to hinder or prevent complete resuspension of the microbeads in the medium when it is subjected to moderate stirring. Under standard culture conditions, the density of the microcarriers is usually between 1.030 and 1.050 g/ml.

The surface of the microbeads is chosen so as to facilitate the adherence of the cells. The matrix of the microbeads is preferably nonrigid so as to provide better preservation of the cells when collisions occur between microbeads. The mean surface available for the adherence of cells is usually between 4000 and 5000 $cm^2$/g of microbeads. These characteristics are found, for example, in cross linked dextran-based microbeads sold under the name Cytodex® (cytodex 1, cytodex 2, cytodex 3), but may also be found in other microbeads, the matrix of which is made of cross linked polystyrene (e.g., Biosilon, Solohill) or of glass (e.g., from Sigma Aldrich).

In the context of the present invention, the microcarrier concentration during the first cell passage is generally reduced to a concentration <1 g/l (in particular when Cytodex™ microbeads like Cytodex™ 1 microbeads are used), whereas in the prior art the microcarriers are used at a concentration of between 1 and 5 g/l. In the process of the invention the concentration is usually ≤0.5 g/l; often between 0.1 and 0.4 g/l, and frequently between 0.1 and 0.3 g/l. These concentrations correspond to the initial microcarrier concentration in the culture medium after cell introduction. The initial microcarrier concentration is therefore generally ≤1 g/l and preferably ≤0.5 g/l; particularly useful values are between 0.1 and 0.4 g/l, and more specifically it is between 0.1 and 0.3 g/l.

The initial amount of cells that is introduced into the culture vessel is chosen such that more than 80% of the microcarriers are colonized by the cells. In order to obtain this degree of colonization, an initial amount of cells that is at least 5 to 10 times greater than the amount of microcarriers present in the culture medium is conventionally introduced into the culture vessel. For example, in the case of a Vero cell production, the initial amount of cells introduced into the culture vessel is generally between $5 \times 10^3$ and $5 \times 10^4$ cells/$cm^2$ of Cytodex™ microcarriers, which represents approximately between 5 and 50 cells per microcarrier. In fact, because the microcarrier concentration in the culture medium during the first cell passage is lower than that which is conventionally used in the prior art, it consequently follows that the initial cell concentration is also lower.

At the end of each cell passage, the cells are detached from the microcarriers in a short period of time (in general less than 30 minutes and preferably less than 15 minutes) by treating the cells with an enzyme solution that has a proteolytic activity (protease). In the context of the invention, the cells are usually detached from the microcarriers in the culture vessel that is used to perform the successive cell passages, which means that all the cell culture phases and all the treatments that are performed on the cells during the successive passages are carried out in one and the same culture vessel.

A possible method for detaching the cells from the microcarriers comprises transferring the cells into a secondary vessel where the enzyme treatment takes place and then reintroducing the cell suspension into the first culture vessel where the successive cell passages take place. This method has the inconvenient to cause the loss of cells during the transfer operations and requires additional material.

The enzyme solution usually contains a serine protease such as trypsin, Pronase® or Dispase®. One can also use papaïn, ficin or collagenase when the microcarriers are cytodex 3 microbeads. Commonly, a trypsin solution is used to detach adherent cells from Cytodex™ microbeads. Preferably, the protease is of nonanimal origin, which indicates that its manufacturing process does not use material of animal origin. The protease is preferably obtained, for example, from plant material, by chemical synthesis, or by genetic recombination using bacteria, yeast, fungi or plants. For instance, an enzyme solution free of any product of animal origin sold by Invitrogen under the trade name TrypLE™ Select or TrypLE™ Express may be used. The protease is produced by fermentation of the *Fusarium oxysporum* DSM 2672 strain or produced by genetic recombination. This protease, the protein sequence of which is described in WO 94/25583, has an enzyme activity similar to trypsin.

In order to facilitate the detachment of the cells, a chelating agent that binds calcium ions (e.g., EDTA, EGTA and citrate) can be added to the enzyme solution. Or, optionally, the adherent cells are treated with a chelating agent before the enzyme treatment. The concentration of protease and, optionally, of chelating agent in the medium and also the temperature at which the enzyme treatment of the cells is carried out (usually between 20 and 38° C.) are set such that more than 80% of the cells are detached from their support in a short period of time (≤30 minutes). Prior to the enzyme treatment, at least half of the culture medium volume is generally withdrawn (usually about ⅔). The proteolytic activity is then neutralized by adding to the medium an inhibitor, generally of peptidic or protein origin, that neutralizes the action of the protease. Preferably the composition of the inhibitor is free of any contaminant of animal origin. For example, recombinant aprotinin or extracts or purified fractions containing a trypsin inhibitor originating from soya beans or from lima bean (Worthington Biochemical) can be used. The medium is preferably stirred during the entire detachment phase of the cells from their microcarriers, except when the culture medium is withdrawn.

The cell suspension obtained is usually quantified with conventional methods assessing the viability and the number of cells. Although a portion of the cell suspension can be withdrawn from the culture vessel, preferably all the cell suspension is used to initiate a subsequent cell passage in the same vessel. In order to increase the number of cells, it is necessary to introduce in the culture vessel at the beginning of each subsequent cell passage (i.e., starting after the detachment phase) an amount of microcarriers that is larger than the amount of microcarriers that was previously introduced. If the same culture medium volume is maintained during the successive cell passages, that amounts to increasing the microcarrier concentration at each cell passage subsequent to the first cell passage. On the other hand, the same microcarrier concentration can be maintained along the successive cell passages if the culture medium volume is increased proportionately at each new cell passage. Preferably, at the beginning of each cell passage subsequent to the first cell passage both the culture medium volume and the microcarrier concentration are increased in the culture vessel in order to enhance cell amplification. By way of example, at each cell passage subsequent to the first cell passage the cells are cultured in a volume of culture medium that is between 1.2 and 3 times larger than the volume in which they were cultured during the previous passage. In the same way, at each cell passage subsequent to the first cell passage the concentration of microcarriers in the culture medium is between 2 and 10 times higher than that which existed during the previous cell passage. In the context of the present invention, there is generally no need to remove the used microcarriers (i.e., microcarriers that have been already been colonized during the preceding passages) at the end of each passage (after the detachment phase). Even though these microcarriers may possibly be recolonized by cells, the amount of used microcarriers originating from the preceding cell passages is not generally taken into account for calculating the amount of microcarriers that has to be introduced at each new passage. The phase of adhesion of the cells to the microcarriers generally lasts between 1 and 10 hours depending on the cell type. After the adhesion phase, it may be advantageous to remove all or part of the culture medium after having allowed the microcarriers to settle out, and to replace it with new medium in order to accelerate cell growth.

Cell culture media for the purpose of the invention can be conventional culture media supplemented with serum of animal origin. Advantageously, however, the culture media contain neither serum nor serum protein. In some preferred embodiments, the culture media is free of any protein of animal origin or even of any product of animal origin. The term "protein or product of animal origin" is intended to mean a protein or a product originating from animals or from humans. Particularly advantageously, the media used for culturing the cells is free of protein or contain very small amounts of proteins in the form of recombinant proteins or proteins extracted from plants (e.g., soya, rice, etc.) or from yeasts. Media for use in the invention will commonly contain low-molecular-weight proteins (≤10 KD) (also called polypeptides) at very low concentrations. The total protein concentration in these culture media is generally ≤15 mg/l measured by the Bradford method. This is the case, for example, for the VP SFM medium sold by InVitrogen, which is suitable for the process according to the invention, in particular for culturing Vero cells. Other suitable media include Opti Pro™ serum-free (InVitrogen), Episerf (InVitrogen), Ex-Cell® MDCK (Sigma-Aldrich), Ex-Cell™ Vero (SAFC biosciences) MP-BHK® serum free (MP Biomedicals), SFC-10 BHK express serum free (Promo cell), SFC-20 BHK express protein free (Promo cell), HyQ PF Vero (Hyclone Ref. SH30352.02) and Hyclone SFM4 Megavir, MDSS2 medium (Axcell biotechnology), Iscove's modified DMEM medium (Hyclone), Ham's nutritive media (Ham's F10, Ham's F12), Leibovitz L-15 medium (Hyclone), ProVero medium (Lonza) and Power MDCK medium (Lonza) that are free of any product of animal origin and which contain little or no proteins.

When the culture medium is free of animal serum or of serum protein or when its protein content is very low (e.g. <15 mg/l according to the Bradford method), a cell protection agent is usually added. It protects the cells against the shear forces that are exerted when the medium is subjected to stirring. The cell protection agents most commonly used have surfactant properties. For example, cell protection agents that can be used in the processes of the present invention include vinyl alcohol polymers (also known as polyvinyl alcohols or PVAs), ethylene glycol polymers (also known as polyethylene glycols or PEGs), 1-vinyl-2-pyrrolidone polymers (also known as polyvinylpyrrolidone or PVP) and poloxamers (which are "block copolymers" of ethylene oxide and propylene oxide having the chemical formula $HO(C_2H_4O)_a(C_3H_6O)_b(C_2H_4O)_aH$, wherein "a" denotes the number of ethylene oxide units and "b" denotes the number of propylene oxide units). These cell protection agents are generally used in a concentration range of between 0.001% and 2% (w/v) in the culture medium. Particularly preferred cell protection agents include poloxamer 188 and PVP. Poloxamer 188 or Pluronic® F68, which has a mean molecular weight of about 8400 daltons and is usually used in the culture medium in a concentration range of between 0.05% and 0.2% (w/v). PVP is also recommended because it stimulates cell growth, as is described in WO 01/40443. PVP is generally used in an average molecular weight range of between 20 KDa and 360 KDa, preferably in an average molecular weight range of between 20 KDa and 40 KDa, at a concentration in the culture medium that is generally between 0.01% and 2% (w/v) and preferably at a concentration between 0.05% and 0.5% (w/v). PVP can also be characterized not only by its molecular weight only but also according to its K value, which takes into account the average molecular weight of a PVP and also the variations in molecular weight on either side of the average value. For the calculation of the K value, reference is made to the equation as defined in the article Cryobiology, 8, 453-464 (1971): the K value is calculated on the basis of the relative viscosity of a 1% solution of PVP according to the formula:

$$\text{Log }\eta\text{rel}/C = 75K_0^2/(1+1.5\,K_0C) + K_0$$

wherein $K = 1000\,K_0$,

C is the PVP concentration in grams per 100 ml of medium, and

η rel is the viscosity of the solution compared with that of the solvent.

PVP suitable for the subject of the invention has a K value that is generally between 18 and 60 and preferably between 26 and 35. By way of example, a culture medium free of product of animal origin with less than 15 mg/l of proteins (according to the Bradford method) (such as VPSFM medium sold by Invitrogen) containing as cell protection agent either a PVP having a K value of about 30 at a concentration of about 0.1% (w/v) or poloxamer 188 at a concentration of about 0.1% (w/v) in the culture medium can be used for producing a stock of Vero cells according to the process of the invention.

The same culture medium is normally used to carry out the successive cell passages, although it may be advantageous to add nutritive supplements such as glucose and/or glutamine during the successive cell passages. Depending on cell requirements, it may also be useful during the cell amplification phases to renew all or part of the culture medium. This is evaluated by means of conventional test methods available to those skilled in the art, such as the measurement of the level of glucose, glutamine, lactates, ammonium ions. This makes it possible to ensure that the cell amplification phase proceeds correctly. In the context of the present invention, except when all or part of the culture medium is withdrawn (for renewal purpose or for reducing the volume of culture medium), the culture medium is usually permanently stirred with an intensity just sufficient to maintain suspension of the microcarriers in the culture medium.

The volume of the culture medium during the first cell passage usually represents between half and ⅕ of the working volume of the culture vessel. In the case of culture vessels with a large capacity (bioreactors of more than 100 liters), the particular configuration of which enables the culturing of cells adherent to microcarriers in a small volume (such as, for example, a bioreactor equipped with a conical-bottomed sedimentation zone), the volume of the culture medium may be smaller (between ⅙ and 1/10, of the working volume of the bioreactor) or even smaller and may represent only 1/20 of the working volume of the bioreactor. As previously mentioned, the culture medium volumes generally increase gradually with each successive cell passage, the last cell passage often being performed in a volume of culture medium that corresponds to at least 70% of the entire working volume of the vessel.

The culture vessel is equipped with a stirring system (e.g., mechanical, by means of a current of air, etc.) for maintaining the microcarriers in suspension in the culture medium and has means to renew the media according to the needs of the cell culture and/or means for testing and/or regulating the temperature, the pH, the oxygen pressure, the gassing optionally with nitrogen or with air, and the metabolites or nutrients (e.g., lactates, glucose, glutamine, ammonium ions, etc.). These devices are well known to those skilled in the art who know how to use them according to the size and the configuration of the vessel used. By way of example, the culture vessel according to the invention may be in the form of spinners or of a bioreactor. When the working volume of the vessel is ≥2 liters, use is normally made of a bioreactor that may be conventionally in the form of a reusable metal tank or a glass tank or, optionally, in the form of a "single use bag" sold, for example, by P. Guerin under the name Nucleo PG-ATMI™. Use may also be made of the Biowave system (Wave Bioreactor™) sold by General Electrics, the STR disposable Bioreactor™ system (Sartorius), the SUB™ system (Hyclone), and the cell ready system (Millipore). In the context of the process according to the invention, the main objective of which is to produce cell batches on an industrial scale, a bioreactor of which the working volume is between 3 liters and 1000 liters can be used. But, preferably, the working volume is between 20 liters and 500 liters.

For the purpose of the invention, "adherent cells" are cells established as lines or cells resulting directly from the extraction of healthy or tumoral animal or human tissues that under the culture conditions used need a solid support in order to multiply and develop normally. They form a single-cell layer on their support owing to the contact inhibition phenomenon. Cells that under the culture conditions used do not need a solid support in order to multiply and that grow in suspension in the culture medium are therefore excluded. The adherent-cell lines can be derived from primary cultures of healthy or tumor cells but also can be obtained by transformation of cells using immortalizing agents, as is the case for the PER.C6 line.

Adherent-cell lines suitable for the subject of the invention include, for example, murine cell lines such as the 3T3, NTCT or WEHI line, hamster cell lines such as the BHK line (in particular the BHK21 line) or the CHO line, canine cell lines such as the MDCK line, porcine cell lines such as the PK15 line, bovine cell lines such as the MDBK line, simian cell lines such as the Vero, LLC-MK2, MA104 or FRHL2 line, and human lines such as the MRC5, 293, PER.C6, Hela, ECV or A 431 line. These adherent cell lines can also be in the form of cell lines transfected with a recombinant vector (e.g., plasmid, virus, etc.) when they are intended for the production of recombinant proteins.

Owing to the process according to the invention, the population of adherent cells can be increased by a factor of at least 40, preferably at least 60, and particularly preferably of at least 100 by carrying out several successive passages in a single culture vessel. This can be done because the process according to the invention makes it possible to increase by between 5 and 40 times, preferably between 10 and 30 times, the surface of the cell support during the successive cell passages carried out in this single vessel. In the prior art methods, a cell amplification of this order is observed using at least two vessels, but more generally three culture vessels of different sizes (see Example 5). The process according to the invention is very advantageous because the same industrial amounts of cells as those obtained by using the prior art methods are also produced in the same time periods, while at the same time reducing the costs related to the use and maintenance of culture vessels as well as the space needed.

The process for producing adherent cells according to the invention can advantageously be carried out by directly introducing into the culture vessel cells that have just been thawed, without recourse to an adaptation period, during which one or more "adaptation" cell passages are conducted (with transfer into a new culture vessel after each passage) in order to "adapt" the cells to more difficult culture conditions, such as culturing in the presence of Cytodex™ microbeads at a low concentration (<0.5 g/l) in the culture medium and/or culturing in media that do not contain serum or that contain very few proteins (≤15 mg/l). By way of example, in the process of the present invention a stock of adherent cells is thawed according to methods well known to those skilled in the art and then the cell suspension obtained is directly introduced into the culture vessel containing the microcarriers in the culture medium. As indicated previously, the microcarrier concentration in the culture medium during the first cell passage is usually ≤0.5 g/l; it is generally between 0.1 and 0.4 g/l and more specifically it is between 0.1 and 0.3 g/l, especially when Cytodex™ microbeads are used. The culture medium also does not need to contain serum or serum proteins. The culture medium can even be completely free of proteins or have very low total protein content, (≤15 mg/l). The stock of frozen cells can originate from a vial (in this case, the amount of cells is generally relatively low, $10^7$ to $5 \times 10^8$ cells) or advantageously originate from a bag that contains up to 100 times more cells. By using frozen bags of large capacity, the large-scale cell production process is accelerated because a culture vessel with a large working volume can be immediately used.

When a cell stock that has been produced using the process of the invention is not sufficient, the cell biomass obtained from a single culture vessel can be increased by transferring the cell population:

either into one or more culture vessels that are used to carry out successive cell passages conventionally, i.e., by transferring, after each cell passage, the cell biomass obtained into a larger culture vessel; or more advantageously into a second culture vessel having a much larger working volume (generally at least 10 times larger, most commonly between 10 and 50 times larger than the preceding vessel) and by repeating the process according to the invention on the cells that have been transferred into this second vessel. By carrying out the process in this way, the number of culture vessels to be used in order to produce industrial batches of cells is even more significantly reduced, as is the space needed.

In order to assess the economic impact of the implementation of the process according to the invention in the context of an industrial-scale production of adherent cells, reference may be made to the conventional scheme for the industrial production of Vero cells intended for the production of poliovirus, as described in Reviews of Infectious Diseases, vol. 6, supplement 2, S341-S344 (1984). The conventional scheme comprises five successive cell passages, the first being carried out in a 1-liter bioreactor, the second in a 5-liter bioreactor, the third in a 20-liter bioreactor, the fourth in a 150-liter bioreactor and, finally, the fifth in a 1000-liter bioreactor. But owing to the process according to the invention, it is possible to carry out the first three cell passages in a single 20-liter bioreactor and then to carry out the last two passages conventionally by transferring the cells into a 150-liter bioreactor and then into a 1000-liter bioreactor. It is also possible to repeat the process according to the invention twice, carrying out the first three cell passages in a single 20-liter bioreactor and then transferring the cells obtained directly into a single 500 or 1000-liter bioreactor where the last two cell passages are carried out. In both cases, the amount of cells obtained is of the same order as that obtained when the conventional, prior art scheme is applied and do not require a longer period of time to be obtained. In the first case a saving of two bioreactors (1 liter and 5 liters) is made, and in the second case a saving of three bioreactors (1 liter, 5 liters and 150 liters) is made (cf. Example 5).

A process for producing adherent cells that is particularly advantageous from an economic standpoint consists of repeating the process according to the invention in two culture vessels of very different size. To this effect, the subject of the invention is therefore:

A process for producing adherent cells, comprising:
a. introducing adherent cells into a first culture vessel that contains microcarriers in a culture medium;
b. amplifying the cells by performing a plurality of cell passages in the first culture vessel, wherein each cell passage subsequent to the first cell passage is carried out by using all or part of the cells produced during the previous cell passage, which cells had been subjected to an enzyme treatment to detach the cells from the microcarriers, and by introducing culture medium and an increasing amount of microcarriers;
c. harvesting the cells obtained during the last cell passage carried out in this first culture vessel after having detached the cells from microcarriers by means of an enzyme treatment;
d. transferring the harvested cells into a second culture vessel that has a larger working volume and contains a culture medium containing microcarriers in a larger amount than the amount of microcarriers that was present during the last cell passage carried out in the first culture vessel;
e. amplifying the cells by performing a plurality of cell passages in the second culture vessel, wherein each cell passage subsequent to the first cell passage is carried out by using all or part of the cells produced during the previous cell passage, which cells had been subjected to an enzyme treatment to detach the cells from the microcarriers, and by introducing culture medium and an increasing amount of microcarriers;
f. harvesting the cell population obtained during the last cell passage carried out in the second culture vessel after having detached the cells from microcarriers by means of an enzyme treatment; and optionally
g. repeating parts d to f in a third culture vessel that has an even larger working volume.

In general the working volume of the second culture vessel is 20 to 50 times greater than the working volume of the first culture vessel.

Advantageously, adherent cells that are introduced in part a) originate from a stock of frozen cells that have been thawed just before being introduced in the first culture vessel.

The process of the invention can also be repeated in two or more culture vessels to produce a biological agent. To this effect, the subject of the invention is therefore:

A process for producing a biological agent from adherent cells, comprising:
a. introducing adherent cells into a first culture vessel that contains microcarriers in a culture medium;
b. amplifying the cells by performing a plurality of cell passages in the first culture vessel, wherein each cell passage subsequent to first cell passage is carried out using all or part of the cells produced during the previous cell passage, which cells had been detached from the microcarriers by means of an enzyme treatment, and by introducing culture medium and an increasing amount of microcarriers;
c. harvesting the cell population obtained during the last cell passage carried out in the first culture vessel after having detached the cells from the microcarriers by means of an enzyme treatment;

d. transferring the harvested cell population into a second culture vessel that has a larger working volume and contains a culture medium containing microcarriers in a larger amount than the amount of microcarriers which was present during the last cell passage carried out in the first culture vessel;

e. amplifying the cells by performing a plurality of cell passages in the second culture vessel, wherein each cell passage subsequent to the first cell passage is carried out by using all or part of the cells produced during the previous cell passage, which cells had been detached from microcarriers by means of an enzyme treatment, and by introducing culture medium and an increasing amount of microcarriers;

f. treating in the second culture vessel the cell population produced during the last cell passage carried out in the second culture vessel such that it produces the biological agent; and g. harvesting the biological agent.

Optionally, the steps d) and e) can be repeated in a third culture vessel before treating the cell population such that it produces the biological agent.

As indicated above, the biological agent which is produced can be, for example, a recombinant protein or a virus such as rabies virus.

A subject of the invention is also the use of the cells which have been produced by means of one of the processes according to the invention for the production of biological agents.

Finally, the invention relates to a process for producing adherent cells in a culture medium that contains microcarriers, wherein a plurality of passages are carried out in a single culture vessel to increase the cell population by a factor of ≥40, preferably by a factor of ≥60 and particularly preferably by a factor of ≥120. The culture vessel used is preferably a bioreactor which has a working volume of at least 20 liters.

Figure 1A:
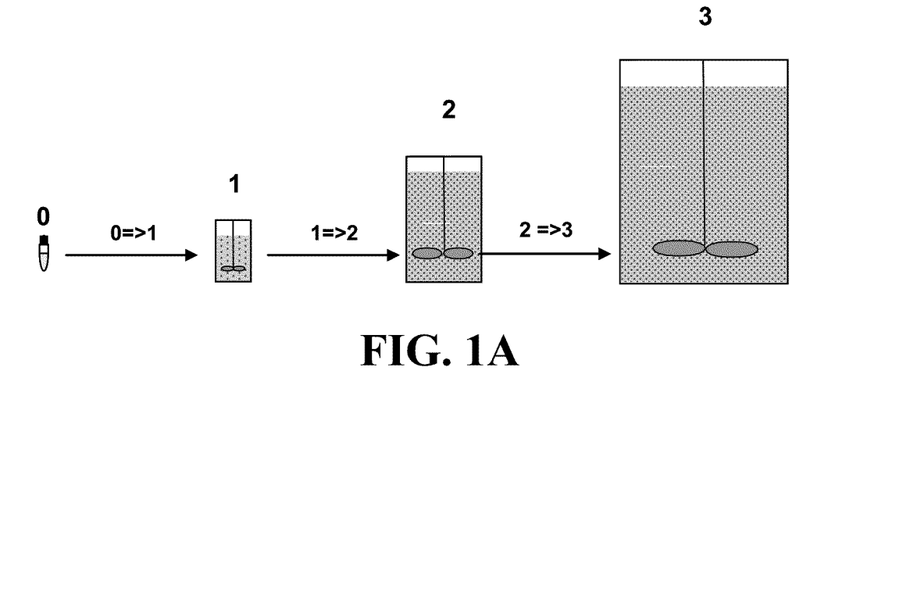
FIGS. 1a and 1b display schematic representations of two processes for amplifying adherent cells on microcarriers by means of several successive passages.
Figure 1B:
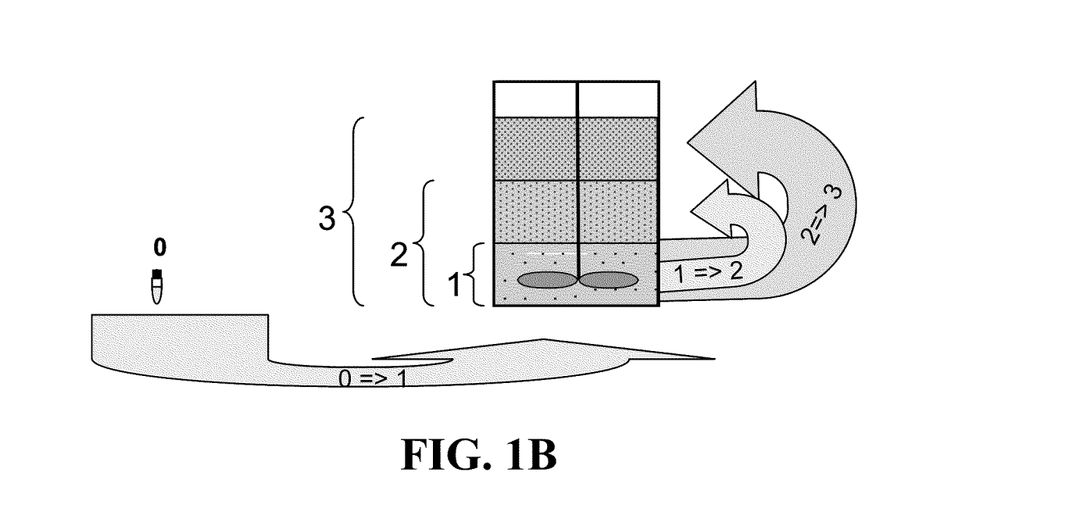

FIG. 1 represents two processes for amplifying adherent cells on microcarriers by means of several successive passages: a) according to the conventional process, the successive cell passages are carrying out in different culture vessels of increasing working volumes, and b) according to the process according to the invention ("all-in-one process") the successive cell passages are carried out in one and the same culture vessel. The cells are in frozen form at stage 0, Step 0→1 corresponds to the transfer of the thawed cells into a bioreactor. Step 1 corresponds to the first cell passage. Step 1→2 corresponds to the transfer of the cell population obtained at the end of the first cell passage after treatment with a proteolytic enzyme to detach cells from their microcarriers either, in the case of process a), into a second bioreactor which has a larger working volume, or, in the case of process b), into the same culture vessel. Step 2 corresponds to the second cell passage. In the case of process b), the second cell passage is generally carried out in a larger culture medium volume and in the presence of a higher microcarrier concentration. Step 2→3 corresponds to the transfer of the cell population obtained at the end of the second cell passage after treatment with a proteolytic enzyme to detach cells from their microcarriers either, in the case of process a), into a second bioreactor which has a larger working volume, or, in the case of process b), into the same culture vessel. Step 3 corresponds to the third cell passage. In the case of process b), the third cell passage is generally carried out in a larger culture medium volume and in the presence of a higher microcarrier concentration than during the second cell passage.

Figure 2A:
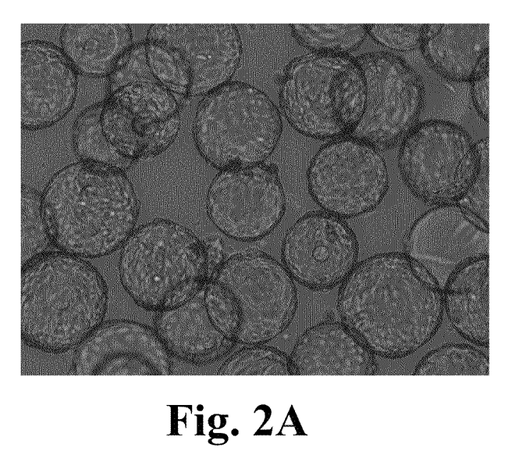
FIGS. 2a and 2b display micrographs of microbeads (20× magnification) after a 8 day period of vero cell culture by carrying out either the "all in one process" (FIG. 2a) or) the "bead-to-bead transfer technology" (FIG. 2b)—(see example 2 for the operating mode).
Figure 2B:
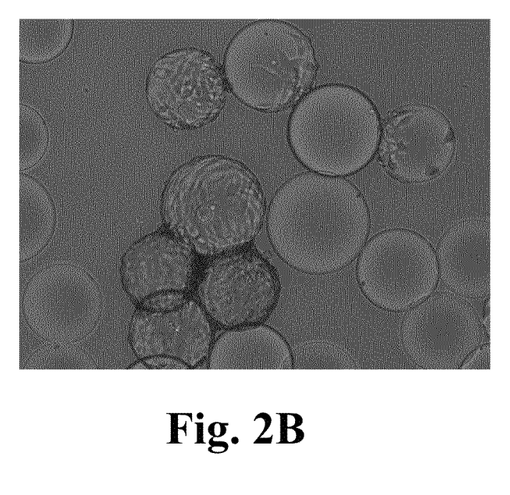

FIG. 2 displays micrographs of microbeads (20× magnification) after a 8 day period of vero cell culture by carrying out either a) the "all in one process" or b) the "bead-to-bead transfer technology"—(see example 2 for the operating mode)

The present invention will be understood more clearly in the light of the following examples which serve to illustrate the invention without however limiting the content thereof.

Example 1

Amplification of the Vero by Carrying Out Three Successive Cell Passages in a Single 2-Liter Bioreactor In this example the role of different parameters such as the initial microbead concentration, the presence or the absence of serum and the nature of the cell protecting agent on the cellular growth were assessed.

1.1) Material Used

Bioreactor:

The studies were performed in disposable glass bioreactors with a 2.4 liter working volume sold by Millipore under the name of "Cell Ready (Mobius)". They are equipped with a pH, pO2 and temperature probes and with a stirring paddle.

Microcarriers:

Cytodex 1 microbeads supplied by GE Healthcare were used. The microbeads were hydrated for 24 hours in a phosphate buffer solution, pH ≈7.4, after having removed the amount necessary to carry out each cell passage. They were then rinsed three times in the same buffer and then sterilized by autoclaving. Just before introduction into the bioreactor, the sterilization buffer was replaced with an equivalent volume of culture medium after settling-out the microbeads. 1 g of cytodex microbeads represents an adhesion surface of about 4400 $cm^2$.

Media Tested:

VPSFM/K30: VPSFM medium (Invitrogen), serum free and free of product of animal origin, supplemented with 0.1% w/v of polyvinylpyrrolidone (PVP) K30 supplied by ISP.

VPSFM/F68: VPSFM medium (Invitrogen) supplemented with 0.1% w/v of poloxamer 188 supplied by BASF.

VPSFM/K30/SVF: VPSFM/K30 medium supplemented with 4% foetal calf serum.

Cells:

Vero cells originating from a bank of cells stored in frozen form at $50 \times 10^6$ cells/ml in a serum-free medium containing 10% dimethyl sulfoxide in cryogenic tubes for freezing cells (Nunc tube ref: 430663, 5 ml).

1.2) Operating Protocol Used to Assess the Role of the "Initial Microbead Concentration" and "The Cell Protecting Agent" in the "All in One Process"

The same protocol was used to assess these two parameters.

Microbead concentrations of 0.1 g/l and 0.3 g/l were tested to assess the effect of a very low microbead concentration during the first cell passage on Vero cell growth.

$66 \times 10^6$ cells in 2 liters of VPSFM/K30 medium containing 0.6 g of microbeads were introduced into a first bioreactor (Bio 1) (which represents an amount of ≈25000 cells/$cm^2$ of adhesion surface and an initial microbead concentration of 0.3 g/l) after having adjusted the regulation parameters (pH between 7.2 and 7.4, $pO_2$ at ≈25% and temperature at 37° C.)

In the same way, $22 \times 10^6$ cells in 2 liters of VPSFM/K30 medium containing 0.2 g of microbeads were introduced into a second bioreactor (Bio 2) (which represents an amount of ≈25000 cells/cm² of adhesion surface and an initial microbead concentration of 0.1 g/l).

At day D3, cells were treated with trypsin according to the following protocol:

After settling out the microbeads, ≈300 ml of the VPSFM/K30 culture medium were left in bioreactor and then ≈300 ml of a 0.025M sodium citrate solution containing 600 mg of recombinant trypsin (ref: Roche 04618734) in phosphate buffer without calcium and magnesium were added. The medium was maintained under a moderate stirring. After having verified that the cells had indeed detached, by means of a test sample (in general, this detachment took place in a period of between 15 and 30 minutes), the action of the trypsin was stopped by adding ≈300 ml of a solution of VPSFM/K30 containing 1 mg/ml of trypsin inhibitor (ref: Sigma T6522). After cell counting, a portion of the cell suspension volume was removed to adjust the remaining amount of cells such that there was ≈25000 cells/cm² of adhesion surface after having introduced either 2.4 g of microbeads (Bio 1) or 0.6 g of microbeads (Bio 2) in a total volume of cell culture medium of 2 liters to carry out the second cell passage. The cell culture medium was renewed twice; a first time 4 to 6 hours after the introduction of naked microbeads, and a second time at day D2. At Day D10, the cells were harvested and counted to assess cell amplification according to the initial microbead concentration into the culture vessel.

The same operating protocol was used (with an initial microbead concentration of 0.3 g/l) to test Poloxamer 188 and PVP K30 as cell protecting agents.

1.3) Operating Protocol Used to Assess the Role of the "Serum" in the "All in One Process"

The same protocol as the one described in paragraph 1.2 was used with the following features:
VPSFM/K30/SVF medium was tested;
the initial microbead concentration was 0.3 g/l; and
the trypsin treatments were made at Days D5 and D8. Prior to the trypsin treatment, the microbeads suspension was rinsed 3 times with ≈600 ml of a "rinse buffer" (PBS 1×C) to remove serum.

1.4) Results

To assess the role of the tested parameters on cellular growth, at regular intervals duplicate samples of the microbead suspension were withdrawn from the bioreactor. The cell concentration was measured with the Nucleocounter (Chemometec®) counting system and the number of cumulative cell generations was also calculated. The amounts of cells and the number of cumulative cell generations observed are given in the tables below according to the tested parameter. The values mentioned in the tables were obtained from the mean values of the duplicate samples that were tested at the mentioned day 1.4.1) "Initial Microbead Concentration" Parameter

| Day | Initial microbead concentration: 0.1 g/l | | Initial microbead concentration: 0.3 g/l | |
|---|---|---|---|---|
| | Amount of cells × 10⁶ | Number of cumulative cell generations*** | Amount of cells × 10⁶ | Number of cumulative cell generations |
| J0 | 22 | 0 | 66 | 0 |
| J3* | 159 | 2.85 | 450 | 2.60 |
| J3** | 66 | 2.85 | 264 | 2.60 |
| J4 | 144 | 3.98 | 522 | 3.58 |
| J5 | 267 | 4.87 | 1053 | 4.60 |
| J6 | 690 | 6.24 | 1905 | 5.45 |
| J7* | 822 | 6.47 | 3243 | 6.21 |
| J7** | 375 | 6.47 | 1077 | 6.21 |
| J10 | 2028 | 8.90 | 3150 | 7.76 |

*before trypsin treatment
**after trypsin treatment and cell concentration adjustment to 25 × 10³ cells/cm² of adhesion surface
***For the calculation of the number of cumulative cell generations, the formula mentioned below was used and it was also taken into account the cell concentration adjustments made at each cell passage:

Number of cell generations = $\frac{\log_{10}\{[cell]Dx/[cell]D0\}}{\log_{10}2}$ Wherein: [cell] Dx is the mean cell concentration of the duplicate samples that were tested at the mentioned day Dx, and [cell] D0 is the mean cell concentration of the duplicate samples that were tested at Day D0.

The amount of cells obtained after three successive cell passages is less important in the bioreactor wherein the "initial microbead concentration" was the weakest (0.1 g/l), but paradoxically the cell population doubling time is faster. The number of cumulative cell generations is indeed higher along all the duration of the test. Surprisingly, a very weak microbead concentration of 0.1 g/l during the first cell passage has no negative impact on the cellular growth. On the contrary, the cells have a tendency to divide themselves more actively than when they are in a bioreactor containing a higher microbead concentration.

1.4.2) "Cell Protecting Agent" Parameter

| Day | protecting agent: PVP (K30) | | protecting agent: Poloxamer 188 | |
|---|---|---|---|---|
| | Amount of cells × 10⁶ | Number of cumulative cell generations*** | Amount of cells × 10⁶ | Number of cumulative cell generations*** |
| J0 | 66 | 0 | 66 | 0 |
| J3* | 450 | 2.60 | 558 | 3.08 |
| J3** | 264 | 2.60 | 264 | 3.08 |
| J4 | 522 | 3.58 | 357 | 3.46 |
| J5 | 1053 | 4.60 | 909 | 4.84 |
| J6 | 1905 | 5.45 | 1215 | 5.26 |
| J7* | 3243 | 6.21 | 2763 | 6.44 |
| J7** | 1077 | 6.21 | 819 | 6.44 |
| J10 | 3150 | 7.76 | 4029 | 8.73 |

*before trypsin treatment
**after trypsin treatment and cell concentration adjustment to 25 × 10³ cells/cm² of adhesion surface The results show that poloxamer 188 or PVP (K30) adding to a serum free culture medium has a similar effect on cell amplification observed after three successive cell passages carried out according to the "all in one process".

1.4.2) "Serum" Parameter

| Day | Serum free culture medium (VPSFM/K30/SVF) | |
|---|---|---|
| | Amount of cells × 10⁶ | Number of cumulative cell generations*** |
| J0 | 66 | 0 |
| J4 | 993 | 3.91 |
| J5* | 1371 | 4.38 |
| J5** | 264 | 4.38 |
| J6 | 375 | 4.79 |

-continued

| Day | Serum free culture medium (VPSFM/K30/SVF) | |
|---|---|---|
| | Amount of cells × $10^6$ | Number of cumulative cell generations*** |
| J7 | 1098 | 6.40 |
| J8* | 1956 | 7.25 |
| J8** | 528 | 7.25 |
| J11 | 2289 | 9.33 |
| J12 | 3242 | 9.83 |

*before trypsin treatment
**after trypsin treatment

These results show that the "process all in one" is also suitable to adherent cells cultivated on microcarriers in a serum free culture medium.

Example 2

Comparison of the Vero Cell Productions Obtained Either by Using the Process According to the Invention (all in One Process) or by Using the "Bead-to-Bead Transfer" Process Vero cell production was compared after two successive cell passages carried out either according to the "all in one process" or according to the "bead-to-bead transfer" process.
2.1) Material Used
Bioreactor:
The studies were performed in glass bioreactors with a 4 liter working volume sold by Sartorius under the name of "Quattro". They are equipped with a pH, pO2 and temperature probes and with a stirring paddle.
Microcarriers: Cytodex™ 1 microbeads supplied by GE Healthcare (see paragraph 1.1)
Cell culture medium: VPSFM/K30 (see paragraph 1.1)
Cells: Vero cells (see paragraph 1.1)
2.2) Operating Protocol
2.2.1) Operating Protocol Used for the "All in One Process"
The same operating protocol as the one described in paragraph 1.2 was applied with the following features:
The culture medium used was VPSFM/K30
The volume of the culture medium remained the same during the two cell passages and was of 4 liters.
The first cell passage was carried out by using a microbead concentration of 0.3 g/l and by introducing an amount of cells such that there was ≈50000 cells/cm² of adhesion surface.
The culture medium was renewed at day D3.
At day D3, the cells were treated with trypsin according to the same operating mode as the one described in paragraph 1.2. After cell counting, ⅔ of the cell suspension volume was removed to adjust the remaining amount of cells such that there was ≈25000 cells/cm² of adhesion surface after introduction of 4.8 g of microbeads (i.e. a microbead concentration of 1.2 g/l) in a total volume of cell culture medium of 4 liters to initiate the second cell passage. The cell culture medium was renewed twice: a first time 4 to 6 hours after the introduction of naked microbeads, and a second time at day D6.
At Day D8, the cells were harvested and counted. The microbead suspension was also analyzed under a microscope to assess the degree of cell expansion on the microbead surface.

2.2.2) Operating Protocol Used for the "Bead-to-Bead Transfer" Process
The same operating protocol was applied to the "bead-to-bead transfer" process except the cells were not treated with trypsin at day D3. At day D3, ⅔ of the microbead suspension volume was removed such that the same proportion of microbeads and cells were removed to be in the same culture conditions as those used in the "all in one process". Then, 4.8 g of microbeads were introduced in a total volume of cell culture medium of 4 liters (which represents a microbead concentration of 1.2 g/l) to initiate the second cell passage in the same way.
2.3) Results
The amounts of cells and the number of cumulative cell generations observed are given in the table below according to the process used. The values mentioned in the tables were obtained from the mean values of the duplicate samples that were tested at the mentioned day.

| | « all in one process » | | « bead-to-bead transfer process » | |
|---|---|---|---|---|
| Day | Amount of cells × $10^6$ | Number of cumulative cell generations*** | Amount of cells × $10^6$ | Number of cumulative cell generations |
| D0 | 264 | 0 | 272 | 0 |
| D1 | 456 | 0.79 | 416 | 0.61 |
| D2 | 792 | 1.58 | 832 | 1.61 |
| D3* | 1508 | 2.51 | 1536 | 2.50 |
| D3** | 456 | 2.51 | 476 | 2.50 |
| D5 | 1592 | 4.32 | 932 | 3.47 |
| D6 | 2532 | 4.99 | 1236 | 3.87 |
| D7 | 3048 | 5.25 | 1400 | 4.05 |
| D8 | 5420 | 6.09 | 2652 | 4.98 |

*before cell concentration adjustement
**after cell concentration adjustment and possibly after trypsin treatment ("all in one process" case only)
***For the calculation of the number of cumulative cell generations see paragraph 1.4.1

During the first cell passage (D0 to D3), the cell growth was similar in the two bioreactors. On the other hand, during the second cell passage (D3 to D8) the cell amplification was weaker in the bioreactor wherein the "bead-to-bead transfer" technology was carried out. At day D8, the amount of cells was ≈2 times weaker than the amount of cells harvested from the bioreactor wherein the "all in one process" was carried out. The results relating to the evolution of the number of cumulative cell generations were in the same way. At day D8, the number of cumulative cell generations is 6.05 for the cells that were amplified according to the "all in one process". The number of cumulative cell generations is only 4.98 for the cells that were amplified according to the "bead-to-bead transfer" process. Therefore, the cells which are cultivated according to the "all in one process" grow more actively. These results are surprising insofar as the "all in one process" requires the use of trypsin, known to be detrimental to cell growth, to carry out the successive cell passages.

These results have been confirmed in two independent experiments that were carried out according to the same operating conditions. The analysis of variance on the number of cumulative cell generations at Day D8 shows a significant difference (p=0.037)

The microscopy analysis of the microbeads at Day 8 showed that the greatt majority of the microbeads were almost covered by cells when the "all in one process" was carried out (see FIG. 2a). On the other hand, only a portion of the microbeads were covered by cells when the "bead-to-bead transfer" process was carried out. The operating mode used when microbeads were added at day D3 (continuous stirring of the medium or intermittent stirring of the medium) did not change the outcome (see FIG. 2b). The following conditions were applied when the medium was intermittently stirred: Once the microbeads were added at day D3, repeated cycles of stirring for 5 minutes followed by a pause for 20 minutes were carried out for 2 hours. The medium was then continuously stirred at the end of the intermittent stirring period.

Example 3

Amplification of Vero Cells by Carrying Out Two Successive Cell Passages in One and the Same 20-Liter Bioreactor 3.1) Procedure
3.1.1) Material Used
Bioreactor:

A 20-liter bioreactor in the form of a single-use bag sold by ATMI under the name Nucleo-20 was used. The pH, $pO_2$ and temperature probes, after having been calibrated and then sterilized by autoclaving, by virtue of the probe holder bags, were installed on the bag according to the standard ATMI protocol: the Kleenpack® connections located, on the one hand, on the bag and, on the other hand, on the probe holder, were connected, and then the probe was introduced inside the bioreactor through the connection thus created.
Microcarriers: Cytodex 1 microbeads supplied by GE Healthcare were used (see paragraph 1.1)
Cell culture medium: VPSFM/K30 (see paragraph 1.1)
Cells: Vero cells (see paragraph 1.1)
3.2) Operating Protocol Six liters of VPSFM/K30 culture medium were introduced into the Nucleo-20 and then 1 liter of a suspension of microbeads containing 4 g of cytodex 1 (which represents an initial microbead concentration of 0.5 g/l after the addition of the cells) was added. After having adjusted the regulation parameters inside the Nucleo-20, such as the temperature at 37° C., the pH at 7.2-7.4 and the $pO_2$ at ≈25%, and subjected the medium to moderate stirring so as to resuspend the microbeads in the culture medium, 500×10⁶ cells, after having been thawed and taken up in 1 liter of VPSFM/K30 culture medium were introduced into the Nucleo. The culture medium was continuously stirred along the duration of the cell culture except when all or part of the culture medium had to be withdrawn (for renewal purpose or for reducing the volume of the culture medium).

At day D2 (2 days after placing in culture), the medium was replaced with new VPSFM/K30 medium.

At day D5, the cells were trypsinized according to the following protocol:

The stirring, the pH regulation and the $pO_2$ regulations were stopped. Only the temperature regulation was maintained. After settling out of the microbeads, ≈31 of VPSFM/K30 culture medium were left in the bioreactor and then ≈3 liters of a 0.025M sodium citrate solution containing 600 mg of recombinant trypsin (ref: Roche 04618734) in phosphate buffer without calcium and magnesium were added. The medium was then again stirred moderately. After having verified that the cells had indeed detached, by means of a test sample (in general, this detachment takes place in a period of between 15 and 30 minutes), the action of the trypsin was stopped by adding ≈3 liters of a solution of VPSFM/K30 containing 1 mg/ml of trypsin inhibitor (ref: Sigma T6522). The suspension of microbeads containing 28 g of cytodex 1 (which represents a microbead concentration of approximately 1.4 g/l in the medium) was added after having adjusted the culture medium volume to 20 liters with the VPSFM/K30 culture medium. The regulation parameters inside the Nucleo-20 were then again adjusted as during the first cell passage. 4 to 6 hours after the introduction of the microbeads, the medium was replaced with new culture medium. The culture medium was replaced with new culture medium for a second time at D7. At D9, the cells were substantially confluent. They were then trypsinized according to the same protocol as that used at D5. The cell suspension obtained makes it possible to measure the level of cell amplification obtained after two cell passages carried out in the same bioreactor.

3.3) Results

In order to monitor the cell growth, at regular intervals duplicate samples of the microbead suspension were withdrawn from the bioreactor. The cell concentration was measured with the Nucleocounter (Chemometec®) counting system. The amounts of cells are given in the table below. The values mentioned in the table are the mean values of the duplicate samples that were tested at the mentioned day.

| Day of culture | Culture volume | Cell concentration in the medium (cell./ml) | Cell concentration on the support (cell/cm² of microbeads) | Amount of cells × 10⁶ |
|---|---|---|---|---|
| D0 | 8 L | 48100 | 21875 | 385*** |
| D1 | 8 L | 73500 | 33400 | 588 |
| D2 | 8 L | 79500 | 36136 | 636 |
| D2 | 8 L | 46500 | 42272 | 744 |
| D5* | 8 L | 235000 | 213600 | 3760 |
| D5** | 20 L | 145500 | 23600 | 2910 |
| D6 | 20 L | 195000 | 31650 | 3900 |
| D7 | 20 L | 474000 | 76950 | 9480 |
| D8 | 20 L | 807000 | 131000 | 16140 |
| D9 | 20 L | 1313000 | 213000 | 26260 |

*before trypsin treatment
**after trypsin treatment and cell adhesion
***represents the initial amount of viable cells seeded After two successive cell passages of Vero cells carried out in the same 20-liter bioreactor, the cell population increased by a factor of 68 after 9 days of culture, whereas the surface of the cell support was increased by a factor of 7.

Example 4

Amplification of Vero Cells by Carrying Out Three Successive Cell Passages in One and the Same 20-Liter Bioreactor 4.1) Material Used The material which was used is identical to the material described in Example 2.

4.2) Operating Protocol

The 3 successive cell passages were carried out according to the same operating protocol as that described in paragraph 3.2 with the following variations:

the first cell passage was carried out by introducing 250× 10⁶ cells in 8 liters of VPSFM/K30 culture medium containing 2 g of cytodex 1 microbeads (which represents an initial microbead concentration of 0.25 g/l);

at day D5, after the first trypsin treatment was made, to carry out the second cell passage, a suspension containing 14 g of cytodex 1 microbeads was added, which represents a microbead concentration of about 1.07 g/l once the volume of the culture medium was adjusted to 13 liters with the VPSFM/K/30 culture medium.

At day D9, after the second trypsin treatment was made, to carry out the third cell passage, a suspension containing 60 g of cytodex 1 microbeads was added, which represents a microbead concentration of about 3 g/l once the volume of the culture medium was adjusted to 20 liters with the VPSFM/K/30 culture medium.

At D12, the cells were substantially confluent. They were then trypsinized according to the same protocol as that used at D5.

The final cell suspension obtained makes it possible to measure the level of cell amplification obtained after three cell passages carried out in the same bioreactor.

The cell amounts and concentrations observed during the culture are represented in the table hereinafter:

| Day of culture | Culture volume | Cell concentration in the medium ($10^6$ cell./ml) | Cell concentration on the support (cell/$cm^2$ of microbeads) | Amount of cells × $10^9$ |
|---|---|---|---|---|
| D0 | 8 | 0.038 | 30230 | 0.26 |
| D1 | 8 | 0.026 | 20684 | 0.18 |
| D2 | 8 | 0.051 | 40572 | 0.36 |
| D5* | 8 | 0.12 | 95465 | 0.84 |
| D5** | 13 | 0.072 | 11688 | 0.93 |
| D6 | 13 | 0.143 | 23214 | 1.85 |
| D7 | 13 | 0.241 | 39123 | 3.13 |
| D8 | 13 | 0.414 | 67207 | 5.38 |
| D9* | 13 | 0.743 | 120616 | 9.65 |
| D9** | 20 | 0.346 | 25064 | 7.72 |
| D10 | 20 | 0.537 | 34870 | 10.74 |
| D11 | 20 | 1.016 | 65974 | 20.32 |
| D12 | 20 | 1.649 | 107077 | 32.98 |

*before trypsin treatment
**after trypsin treatment and cell adhesion

After three successive cell passages of Vero cells carried out in the same 20-liter bioreactor, the cell population increased by a factor of 126 at the end of 12 days of culture, whereas the surface of the cell support was increased by a factor of 30.

Example 5

Comparison of the Production of Vero Cells Using Either the Process According to the Invention (the Successive Cell Passages are Carried Out in One and the Same Bioreactor) or the Conventional Cell Expansion Process (the Successive Cell passages are Each Time Carried Out in Different Bioreactors of Greater Size)

5.1) Protocol

The production of Vero cells was studied and compared by carrying out either three successive cell passages in a single 20-liter bioreactor according to the protocol described in Example 4 and using an initial amount of $250 \times 10^6$ cells originating directly from a bank of frozen cells, or three successive cell passages in different stainless steel bioreactors, the first in a 2-liter bioreactor, the second in a 7-liter bioreactor and the third in a 28-liter bioreactor. The experimental conditions of the conventional process which were used are the following:

The Vero cells after thawing were first of all adapted to their culture conditions by carrying out an initial passage in Cell Factories (CF10) by introducing $40 \times 10^3$ cells per $cm^2$ of adhesion surface area in 2 liters of VPSFM/K/30 culture medium. After approximately 5 days of culture, the cell population obtained was harvested after a trypsin treatment step. The cell population harvested is used to seed a bioreactor with a working volume of 2 liters containing a suspension of 2 g of cytodex 1 microbeads in 2 liters of VPSFM/K/30 culture medium (concentration 1 g/l). After having tested and adjusted the regulation parameters, such as the temperature at 37° C., the pH at 7.2-7.4 and the $pO_2$ at ≈25%, and subjected the medium to moderate stirring, the 2-liter bioreactor was seeded with, on average, $220 \times 10^6$ cells. At D3, the culture medium was replaced with new culture medium. At D4, the substantially confluent cells were trypsinized and then transferred with the used microcarriers into a 7-liter bioreactor containing 7 liters of VPSFM/K/30 culture medium to which 14 g of cytodex 1 microbeads were added beforehand, which represents a microbead concentration of approximately 2 g/l. At D6, the culture medium was replaced with new culture medium. At D8, the substantially confluent cells were trypsinized and then transferred in the same way into a 28-liter bioreactor containing 28 liters of VPSFM/K/30 culture medium to which 70 g of cytodex 1 microbeads were added beforehand, which represents a microbead concentration of approximately 2.5 g/l. At D10, the culture medium was replaced with new culture medium. At D11, the substantially confluent cells were trypsinized and then harvested and counted.

5.2) Results

In order to monitor the cell growth, at regular intervals duplicate samples of the microbead suspension were withdrawn from the bioreactor. The cell concentration was measured with the Nucleocounter (Chemometec®) counting system. The amounts of cells are given in the table below. The values mentioned in the table are the mean values of the duplicate samples that were tested at the mentioned day

| | "All in one" process, 1 single 20-liter bioreactor | | Conventional process, 3 bioreactors (4, 7 and 28 liters) | |
|---|---|---|---|---|
| Day | Amount of cells × $10^6$* | Level of amplification | Amount of cells × $10^6$** | Level of amplification |
| D0 | 253 | | 220 | |
| D1 | 162 | 0.64 | 446 | 2.03 |
| D2 | 300 | 1.18 | 874 | 3.97 |
| D4 | 832 | 3.29 | 2017 | 9.17 |
| D5 | 1024 | 4.05 | 1499 | 6.59 |
| D6 | 1426 | 5.64 | 2763 | 12.56 |
| D7 | 2448 | 9.68 | 4494 | 20.43 |
| D8 | 4242 | 16.77 | 7251 | 32.96 |
| D10 | 10740 | 42.45 | 16567 | 75.30 |
| D11 | 20320 | 80.32 | 32056 | 145.71 |
| D12 | 29140 | 115.18 | | |

*the amounts expressed are the average values obtained on 8 different tests which were carried out.
**the amounts expressed are the average values obtained on 3 different tests which were carried out.

Using the "all in one" process, more than 29 billion cells are on average obtained after 12 days of culture after having introduced on average 253 million directly thawed cells into a 20-liter bioreactor, i.e. an average level of cell amplification of 115. Using the conventional process, 32 billion cells are on average obtained after 11 days of culture after having initially introduced on average 22 million cells into a 2-liter bioreactor, i.e. an average level of cell amplification of 145. The available cell support surface was increased by a factor of 30 in the two processes, but required the use of three bioreactors in the case of the conventional process. The amount of cells obtained with the conventional process is slightly greater. This comes from the fact that the cells that were used to implement the "all in one" process and the conventional process were not in the same physiological conditions. The cells that were used to seed the 20-liter bioreactor in the case of the "all in one" process had just been thawed, whereas the cells used to seed the 2-liter bioreactor were much more vigorous since they had been cultured beforehand in a Cell factory. The results at D1 show this very clearly; in the all in one process, the decrease of about 40% in the number of cells at D1 is a result of the conventional "post-thaw lag" phenomenon. During the same period of time, the cells which had been cultured beforehand in a Cell factory multiplied in the conventional process (the cell population doubled). Despite the initial culture conditions that are clearly unfavourable in the "all in one" process, it is noted that, at the end of the culture, there is in the end very little difference between the amounts of cells harvested in the two processes. It is concluded that, if the initial culture conditions had been the same in the two processes tested, the same amounts of cells and the same levels of cell amplification would have been obtained. The "all in one" process is therefore very advantageous compared with the conventional process since the same amount of cells is produced in the same period of time, with economy of means.

Example 6

Amplification of Vero Cells by Carrying Out Three Successive Cell Passages in One and the Same 200-Liter Bioreactor 6.1) Material Used With the exception of the bioreactor, which, in the present case, is a 200-liter single-use bag sold by ATMI under the name Nucleo-200, the material which was used is the same as that which is described in Example 3.

6.2) Operating Protocol

The operating protocol used is similar to that which is described in Example 3, with the following modifications:

The Vero cells, after having been thawed, were placed in culture beforehand in two Cell Factories (CF10) in a proportion of $40 \times 10^3$ cells per $cm^2$ of adhesion surface and 2 liters of culture medium per CF10. After 5 days of culture, the cell population was harvested after a trypsin treatment step and was subsequently used to seed the Nucleo-200.

The first cell passage in the Nucleo-200 was carried out by introducing $2.2 \times 10^9$ cells in 50 liters of VPSFM/K/30 culture medium containing 25 g of cytodex 1 microbeads (which represents an initial microbead concentration of 0.5 g/l). At day D3, the culture medium was replaced with new culture medium. At day D4, the cells were trypsinized according to the protocol of Example 2, leaving ≈20 liters of medium in the Nucleo, and then adding ≈20 liters of a 0.025M sodium citrate solution containing 3000 mg of recombinant trypsin in a phosphate buffer containing neither calcium nor magnesium. After detachment of the cells, the action of the trypsin was stopped by adding 20 liters of a solution of VPSFM/K/30 containing 1 mg/ml of trypsin inhibitor.

The second cell passage was carried out in the same Nucleo-200 by adding to the entire cell population obtained a suspension of microbeads containing 130 g of cytodex 1, which represents a microbead concentration of approximately 1 g/l once the total volume of the medium was adjusted to 130 liters with the VPSFM/K/30 culture medium. The culture medium was replaced on two occasions: the first just after adhesion of the cells to the microbeads, the second at D6. At day D7, the cells were again trypsinized according to the same protocol as that used at D4.

The third cell passage in the same Nucleo-200 was carried out by adjusting the cell population so that there was a concentration of 20000 cells/cm2 of adhesion surface after adding 450 g of cytodex 1 microbeads in a total volume of medium adjusted to 180 liters with the VPSFM/K/30 culture medium (which represents a microbead concentration of approximately 2.5 g/l). Similarly, the culture medium was also replaced on two occasions: the first just after adhesion of the cells to the microbeads, the second at D10. At day D11, the cell population obtained after the three successive cell passages carried out in the same bioreactor was quantified. The level of cell amplification can thus be measured.

6.3) Results

The cell amounts and concentrations observed during the culture are represented in the table below:

| Day of culture | Culture volume | Cell concentration in the medium ($10^6$ cell./ml) | Cell concentration on the support (cell/$cm^2$ of microbeads) | Amount of cells × $10^9$ |
| --- | --- | --- | --- | --- |
| D0 | 50 L | 0.038 | 17580 | 1.93 |
| D1 | 50 L | 0.034 | 15455 | 1.71 |
| D2 | 50 L | 0.07 | 31818 | 3.50 |
| D3 | 50 L | 0.147 | 66818 | 7.35 |
| D4* | 50 L | 0.162 | 103000 | 11.34 |
| D4** | 130 L | 0.114 | 25900 | 14.81 |
| D5 | 130 L | 0.135 | 30600 | 17.55 |
| D6 | 130 L | 0.275 | 62500 | 35.75 |
| D7* | 130 L | 0.552 | 125455 | 71.76 |
| D7*** | 180 L* | 0.212* | 19273* | 38.16* |
| D8 | 180 L | 0.329 | 29900 | 59.22 |
| D9 | 180 L | 0.646 | 58727 | 116.28 |
| D10 | 180 L | 1.1 | 100000 | 198 |
| D11 | 180 L | 1.5 | 136364 | 270 |

*before trypsin treatment
**after trypsin treatment and cell adhesion
***after trypsin treatment and adjustment of the cell population in order to have a cell concentration of 20 000 cells/$cm^2$ of adhesion surface.

After three successive cell passages of Vero cells carried out in the same 200-liter bioreactor, the cell population increased by a factor of 140 after 11 days of culture, whereas the surface area of the cell support was increased by a factor of 18.

Amplification of Vero cells, according to the "all in one process" was also carried in one single disposable bioreactor of 500 liters sold by ATMI under the name of nucleo-500. Two successive cell passages were performed in the same bioreactor. The levels of cell amplification were in the same order to those obtained in 200-liter bioreactors, which shows that the process according to the invention is suitable at a very large scale.

Example 7

Production of Rabies Virus from a Batch of Cells that was Obtained by Carrying Out Three Successive Cell Passages in One and the Same 200-Liter Bioreactor The batch of cells was produced using the same protocol as that which was described in Example 6.

At day D11, the culture medium was replaced with a VPSFM-based viral infection medium and then the cells were infected with the Pitman Moore strain of rabies virus from the Wistar Institute at a multiplicity of infection of 0.01. The same regulation parameters relating to temperature, pH, $pO_2$ and stirring used for the cell culture were conserved, and adjusted for virus production. The viral infection medium was renewed at day D3, after viral infection, and then the culture supernatants were harvested in order to measure the infectious titers at days D7, D10 and D14 after viral infection. After each viral harvest, new viral infection medium was again added. The infectious titers in the culture supernatants were measured by means of a conventional immunofluorescence test on BHK21 cells. Serial dilutions were prepared for each of the culture supernatants tested and then each dilution was distributed into 10 wells of a 96-well microplate. Two series of tests were carried out in parallel. A suspension of BHK21 cells was then added to each of the wells.

The cells were incubated for 48 hours at 37° C. under 5% $CO_2$. After 48 hours, the wells were covered with a cell layer which was then fixed with acetone. After having removed the acetone and dried the microplates, 50 µl of a $1/70^{th}$ dilution of a monoclonal antibody directed against rabies virus (FDI Fujirebio Diagnostics-Ref 800092) was added. After incubation for one hour followed by several rinses, the microplates were analyzed under a fluorescence microscope. A well is considered to be positive once specific fluorescence is observed in at least one cell. BHK21 cells cultured in the absence of rabies virus were used as a negative control, and BHK21 cells cultured in the presence of a reference rabies virus strain was used as a positive control. The infectious titers of rabies viruses contained in the culture supernatants tested were determined according to the Spearman-Karber method and expressed in $\log_{10}$ cell culture infectious dose 50% (CCID 50) units. The infectious titers obtained in the culture supernatants that were observed were about 7.0 $\log_{10}$ CCID 50.

What is claimed is:

1. A process for producing adherent cells comprising:
    a) introducing a suspension of adherent cells into a culture vessel containing microcarriers in a culture medium, wherein the culture vessel is in direct physical contact with the culture medium;
    b) amplifying the cells by performing a plurality of cell passages in the same culture vessel, wherein each cell passage subsequent to the first cell passage is carried out:
        i) by retaining in the culture vessel all or part of the cells produced during the previous cell passage after having subjected the cells to enzyme treatment in the culture vessel to detach the cells from microcarriers without removing the all or part of the cells produced during the previous cell passage from the culture vessel, and
        ii) by introducing culture medium and an increasing amount of microcarriers into the culture vessel; and
    c) harvesting the cells produced during the last cell passage, optionally after having subjected the cells to enzyme treatment to detach cells from microcarriers.

2. A process for producing a biological agent from adherent cells, comprising:
    a) introducing a suspension of adherent cells into a culture vessel containing microcarriers in a culture medium;
    b) amplifying the cells by performing a plurality of cell passages in the same culture vessel wherein each cell passage subsequent to the first cell passage is carried out:
        i) by using all or part of the cells produced during the previous cell passage after having subjected the cells to enzyme treatment to detach the cells from microcarriers; and
        ii) by introducing culture medium and an increasing amount of microcarriers;
    c) treating the cells produced during the last cell passage such that it produces the biological agent, wherein said treating is carried out in the same culture vessel as the one used to amplify the cells; and
    d) harvesting the biological agent.

3. The process as claimed in claim 2, wherein the biological agent is an infectious agent and wherein the treatment of the cells in part c) is carried out by infecting the cells with said infectious agent in an infection medium.

4. The process as claimed in claim 3, wherein the infectious agent is rabies virus and wherein the infection medium is a viral infection medium free of any product of animal origin.

5. The process as claimed in claim 1, wherein the number of cell passages carried out in the same culture vessel is 2, 3 or 4.

6. The process as claimed in claim 1, wherein the microcarrier concentration in the culture medium during the first cell passage is <1 g/l.

7. The process as claimed in claim 1, wherein the enzyme treatment employs a solution containing a proteolytic enzyme.

8. The process as claimed in claim 1, wherein each cell passage subsequent to the first cell passage is carried out by increasing the volume of the culture medium.

9. The process as claimed in claim 1, wherein the first cell passage is carried out in a volume of culture medium that is between ⅕ and half the working volume of the culture vessel.

10. The process as claimed in claim 1, wherein the culture medium is free of serum of animal origin.

11. The process as claimed in claim 1, wherein the culture medium is free of product of animal origin.

12. The process as claimed in claim 1, wherein the protein concentration in the culture medium is ≤15 mg/l.

13. The process as claimed in claim 1, wherein the culture medium contains a cell protection agent.

14. The process as claimed in claim 13, wherein the cell protection agent is a polyvinylpyrrolidone or a poloxamer.

15. The process as claimed in claim 1, wherein the culture vessel is a bioreactor that has a working volume of between 3 and 3000 liters.

16. The process as claimed in claim 15, wherein the culture vessel is a bioreactor that has a working volume of between 20 and 500 liters.

17. The process as claimed in claim 15, wherein the culture vessel is a disposable bioreactor.

18. The process as claimed in claim 1, wherein the adherent cells are Vero cells.

19. The process as claimed in claim 1, wherein the cells harvested in part c) contains at least 60 times more cells than the number of cells that were initially introduced in part a), and wherein the cells are Vero cells.

20. A process for producing adherent cells comprising:
    a) thawing a stock of adherent cells, and then
    b) subjecting the thawed adherent cells to the process as claimed in claim 1.

21. The process for producing cells adherent to microcarriers as claimed in claim 1, further comprising:
    a) transferring the harvested cells after having subjected the cells to enzyme treatment to detach cells from microcarriers, into a second culture vessel the working volume of which is larger than the working volume of the first culture vessel and that contains a culture medium containing microcarriers in a larger amount than the amount of microcarriers that was present during the last cell passage carried out in the first culture vessel from which the cells were harvested, and
    b) performing parts b) and c) as claimed in claim 1 to the cells transferred into the second culture vessel.

22. The process for producing adherent cells according to claim 1, wherein the amount of cells produced is increased by a factor ≥60, and wherein the cells are Vero cells.

23. The process as claimed in claim 7, wherein the proteolytic enzyme is trypsin.

* * * * *